United States Patent
Vazquez et al.

(10) Patent No.: US 6,525,027 B2
(45) Date of Patent: Feb. 25, 2003

(54) USE OF RIBOSE SUPPLEMENTATION FOR INCREASING MUSCLE MASS AND DECREASING BODY FAT IN HUMANS

(75) Inventors: Lou Vazquez, Denver, CO (US); Scott Hagerman, Wyoming, MN (US); Terri L. Butler, Kirkland, WA (US)

(73) Assignee: Bioenergy Inc., Ham Lake, MN (US)

(*) Notice: Subject to any disclaimer, the term of this patent is extended or adjusted under 35 U.S.C. 154(b) by 0 days.

(21) Appl. No.: 09/766,858

(22) Filed: Jan. 19, 2001

(65) Prior Publication Data

US 2002/0035069 A1 Mar. 21, 2002

Related U.S. Application Data

(60) Provisional application No. 60/177,139, filed on Jan. 20, 2000.

(51) Int. Cl.[7] .................. A61K 31/70; A61K 31/495
(52) U.S. Cl. ..................... 514/23; 514/52; 514/53; 514/249; 514/561; 514/565; 426/653
(58) Field of Search .............................. 514/23, 52, 53, 514/54, 249, 561, 565; 426/653

(56) References Cited

U.S. PATENT DOCUMENTS

| | | | | |
|---|---|---|---|---|
| 4,312,856 A | * | 1/1982 | Korduner et al. | 424/145 |
| 5,114,723 A | * | 5/1992 | Stray-Gundersen | 426/74 |
| 5,294,606 A | * | 3/1994 | Hastings | 514/53 |
| 5,397,786 A | * | 3/1995 | Simone | 514/300 |
| 6,159,942 A | | 12/2000 | St. Cyr et al. | 514/23 |
| 6,159,943 A | | 12/2000 | Butler et al. | 514/23 |
| 6,192,043 B1 | | 2/2001 | Rochberger | 370/351 |
| 6,192,942 B1 | | 2/2001 | Hsieh et al. | 138/137 |
| 6,218,366 B1 | | 4/2001 | St. Cyr et al. | 514/23 |
| 6,296,892 B1 | * | 10/2001 | Elseviers et al. | 426/653 |
| 6,429,198 B1 | * | 8/2002 | St. Cyr et al. | 514/23 |

OTHER PUBLICATIONS

Gross, M., et al., "Metabolism of D–Ribose Administered Continuously to Healthy Persons and to Patients with Myoadenylate Deaminase Deficiency", *Klinische Wochenschrift, 67*, pp. 1205–1213, (1989).

Gross, M., et al., "Ribose administration during exercise: effects on substrates and products of energy metabolism in healthy subjects and a patient with myoadenylate deaminase deficiency", *Klinische Wochenschrift, 69*, pp. 151–155, (1991).

Hoeger, W. W., et al., "Four–week supplementation with a natural dietary compound produces favorable changes in body composition", *Advances in Therapy, vol. 15, No. 5, No. 1999139301*, 305–14, (Sep.–Oct. 1998).

Steele, I.C., et al., "A double–blind, palcebo controlled, crossover trial of D–ribose in McArdle's disease", *J. of the Neurol. Sciences, vol. 136 (1–2), AN 96253803*, 174–7, (Mar. 1996).

Stone, M.H., et al., "Effects of in–season (5 weeks) creatine and pyruvate supplementation on anaerobic performance and body composition in American football players", *Int'l. J. Sport Nutrition, vol. 9, No. 2, AN1999290802*, 145–65, (1999).

Tullson, P.C., et al., "Adenine Nucleotide Syntheses in Exercising and Endurance–trained Skeletal Muscle", *The American Journal of Physiology, 261 (2)*, pp. C342–C347, (1991).

Tullson, P.C., et al., "IMP Metabolism in Human Skeletal Muscle After Exhaustive Exercise", *The American Journal of Physiology*, pp. 146–152, (1995).

* cited by examiner

Primary Examiner—Samuel Barts
Assistant Examiner—Devesh Khare
(74) Attorney, Agent, or Firm—Schwegman, Lundberg, Woessner & Kluth, P.A.

(57) ABSTRACT

Ribose administered to humans performing weight-training exercise provides more rapid increase in muscle mass and decrease in body fat than weight-training exercise without ribose.

6 Claims, 1 Drawing Sheet

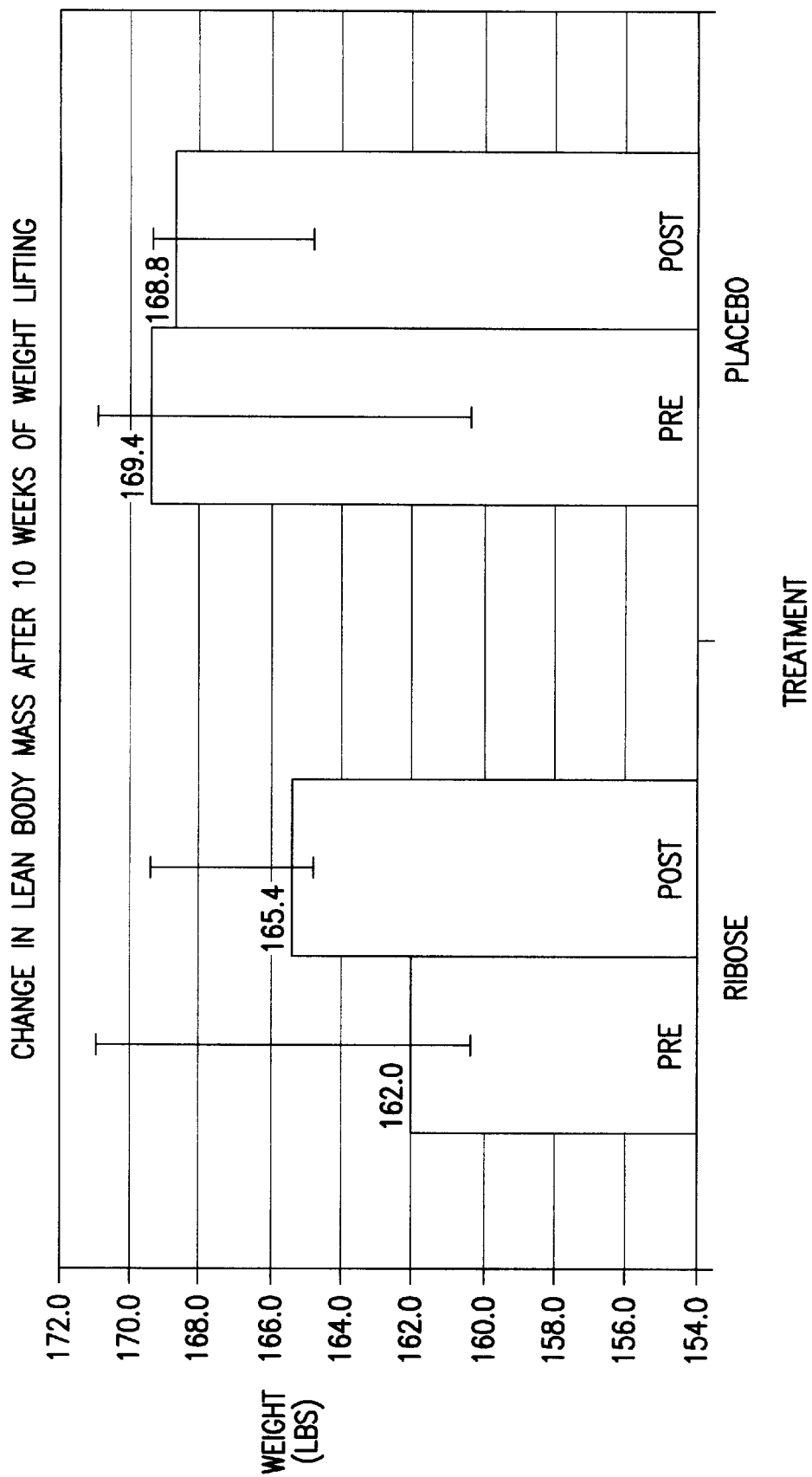

USE OF RIBOSE SUPPLEMENTATION FOR INCREASING MUSCLE MASS AND DECREASING BODY FAT IN HUMANS

RELATED APPLICATIONS

This application claims the benefit of U.S. Provisional Application No. 60/177,139 filed Jan. 20, 2000 under 35 U.S.C. 119(e).

FIELD OF THE INVENTION

The present invention relates to methods and compositions for supplementing the diet of humans performing weight-training exercise in order to increase muscle mass and decrease body fat.

BACKGROUND OF THE INVENTION

Athletes depend on exercise regimens to build muscle mass and reduce body fat in order to give greater definition to muscular development, which is important in body building competitions. Even non-athletes may use exercise regimens to build muscle mass and reduce body fat in order to appear more healthy and fit.

In the area of diet supplementation previous research has shown that creatine in particular, but also L-carnitine, and pyruvate can improve performance for body-builders and other athletes. Effective supplementation can play a critical role in performance and is frequently the determining factor for the athletes who win competitions. Because of the importance of this area to athletes across sports as well as animal trainers, a great deal of research in the area has been fostered. For example it has been found that supplementation with creatine led to increases in the amount of weight lifted via bench press and squats in resistance-trained men, increased handgrip strength and dorsiflexion ankle strength in patients with neuromuscular disease, and increased strength and better sprint performance in football players.

New findings in the area of supplementation are of great interest. For example, it is unknown to what extent various additives may substitute for, replace, show synergistic effects or interfere with the benefit derived from a supplement given alone. This was the motivating factor for pursuing these investigations and revealing the results in this invention.

SUMMARY OF THE INVENTION

The present invention relates to methods and compositions for supplementing the diet of humans performing weight-training exercise in order to increase fat-free mass more rapidly than exercise without the supplements. The present invention provides ribose, alone or in combination with other carbohydrates, electrolytes, enzymes, or other ingredients to increase muscle mass and decrease body fat in humans. The supplement is to be used in conjunction with a preferred regimen of weight-training exercise in order to achieve the desired results more rapidly than with exercise alone.

Preferably, D-Ribose is taken orally in a dose from 0.5 to 40 grams, more preferably 2 to 20 gm, most preferably 3 to 8 gms. Most preferably the D-Ribose is administered just before and just after the exercise regimen. It is preferred that the D-Ribose be administered daily, whether or not the subject is exercising that day. It is preferred that the daily dose be divided into two doses. Additive effects may be obtained by combining the D-Ribose with creatine. Still more additive effects may be obtained by combining the D-Ribose and creatine with L-carnitine, pyruvate, magnesium and chromium picolinate.

The preferred weight-training exercise regimen includes repetitions of contraction of leg, arm, abdominal and back muscles.

DESCRIPTION OF THE DRAWINGS

FIG. 1 shows the changes in lean body mass after 10 weeks of weight lifting

DETAILED DESCRIPTION OF THE INVENTION

It is common knowledge that in order to build muscle and reduce body fat, that is, to increase fat-free mass, it is well known that it is necessary to work the muscles through some form of exercise. With time, muscle mass will increase and body fat will disappear provided that the exercise is strenuous enough and the larger body muscles are exercised. It has now been found that by taking a supplement of D-Ribose and following a preferred regimen of weight-training exercise, the increase in muscle mass and decrease in body fat mass can be achieved more rapidly than with the preferred exercise regimen alone.

It is known that when oxygen demand in the muscles exceeds supply energy levels quickly become depleted. Aerobic metabolism is replaced by less efficient anaerobic metabolism for the production of adenosine triphosphate (ATP). ATP is needed by the cells of the body to maintain function and health so, when under anaerobic conditions the production of ATP is slowed, cellular and tissue function can suffer. As disclosed in U.S. Pat. No. 6,159,942, ribose has been found to be useful for enhancing energy production in healthy humans during intense anaerobic exercise and useful as well in patients with ischemic heart disease. In addition, it is disclosed in U.S. Pat. No. 6,159,943 that ribose can prevent and alleviate muscle soreness and cramping in healthy exercising humans and patients with emphysema. Now, it is herein disclosed that, in spite of not fully understanding the mechanisms by which it might operate, it has been discovered that ribose supplementation, alone or with other supplements, in conjunction with a preferred exercise regimen, can increase muscle mass and decrease body fat more rapidly than with the preferred exercise regimen alone.

This invention provides ribose for use in combination with a preferred weight-training exercise regimen for more rapid increase in muscle mass and decrease in body fat. This invention also provides ribose in combination with creatine, or magnesium, or pyruvate or chromium picolinate. This invention also provides doses and protocols for maximum beneficial effect.

Ribose is a simple 5-carbon sugar, with a slightly sweet taste. It is a white to light yellow crystalline powder. The amount necessary to have the desired effects on increase in muscle mass and decrease of body fat can be between 0.5 and 40 gm per day. The more preferred dose is 2 to 20 gm. A still more preferred dose is 3 to 8 gm. The most preferred dose is around 10 grams per day taken in 5 gram doses before and after workout sessions. The ribose can be ingested directly, sprinkled on food, or mixed in a liquid such as water, juice, coffee, or tea. Ribose can also be ingested as part of an energy bar or other functional food.

The supplements creatine, L-carnitine, pyruvate, magnesium and chromium picolinate when combined with ribose, provides slight incremental improvements over ingestion of ribose alone.

The following examples are included to demonstrate the preferred embodiment of the invention. D-ribose is the preferred embodiment, however, to those skilled in the art it is known that certain pentoses such as xylitol and ribulose are readily converted to D-Ribose in vivo. Therefore, the term "ribose" is intended to include D-Ribose and such precursors thereof. It should be appreciated by those skilled in the art that the methods and dosages in the examples that follow represent methods and dosages discovered by the inventors to function well in the practice of this invention, and thus can be considered to constitute preferred modes for its practice. However, those skilled in the art should, in light of the present disclosure, appreciate that many changes can be made in the specific embodiments that are disclosed and still obtain a like or similar result without departing from the concept and scope of the invention. All such changes are considered to be within the spirit, scope, and concept of the invention as defined by the appended claims.

EXAMPLE 1

Rapid Increase in Muscle Mass and Decrease in Body Fat

The study subjects were healthy males, ages 18 to 40, with previous weight training experience. The subjects were supplement-free for at least the past three months and had a body composition in the 25th percentile or lower, according to ACSM's Guidelines for Exercise Testing and Prescription, 5th Ed. Pages 111–112.

The duration of the study was 10 weeks and included a supplementation regime of D-Ribose or D-Glucose as placebo control, combined with resistance weight training. The subjects were divided into two matched groups, four subjects received D-Ribose and two subjects received placebo.

Baseline testing was conducted before training and supplementation. Prior to any testing the subjects were required to read and sign an informed consent document. Subject information to be collected prior to the start of the exercise regimen included age, height, weight, body composition and performance measures. The body composition was determined by hydrostatic weighing and skinfold measurements to determine beginning percentage muscle mass and percentage body fat.

Initial performance measures were individualized to each subject. The maximum weight each subject could lift once (1RM) was determined for the bench press and the squat lift. The maximal repetitions that each subject was able to lift of his own body weight was determined. Each subject performed as many repetitions as possible, followed by a one-minute rest and then repeated. The sets were continued until no weight could be lifted, limited by a maximum of 10 sets.

There were four training sessions per week. At each training session, the subject was accompanied by a supervisor to ensure proper lifting technique, safety and efficiency of the training session. D-Ribose or placebo at a dose of 5 gm was taken one-half hour before and one-half after the training session. On the three days per week when the subjects were not trained, the subjects were allowed to consume the supplement at their convenience. Dietary recalls were also kept on Tuesday, Wednesday and Thursday of each week, but not dietary requirements were imposed.

The amount of weight lifted was based on the 1RM performance done during pre-testing. The schedule was:

Weeks 1–4: 60% of 1RM, 3 sets of 15–20 reps
Weeks 5–7: 75%–85% of 1RM, 3 sets of 10–12 reps
Weeks 8–10: 90% of 1RM, 3 sets of 5–8 reps The lifting sessions were designed to exercise mainly the largest muscles of the body, that is, arm, leg, abdominals and back. All lifting sessions were preceded by warm-up sets of 20 repetitions at low weights. After week 4, the weight to be lifted was increased when the subject was able to do the maximum number of reps for all three sets. There was a 2-minute rest between each set and a 5 minute rest between each exercise. The lifting sessions were as follows:

TABLE I

| Day 1 | Day 2 | Day 3 | Day 4 |
|---|---|---|---|
| WEEKS 1–4 | | | |
| Abs | Abs | Abs | Abs |
| Calves | Calves | Calves | Calves |
| Triceps Extension | Back Extensions | Lateral Raises | Front Squat |
| Dumbbell Flys | Lunges | Bench Press | Leg Extension |
| Hammer Curl | Bent Kick Crosses | Bicep Curl (Db) | Leg Curl |
| Seated Rows | Leg Press | Lat Pulldown (front) | |
| WEEKS 5–7 | | | |
| Abs | Abs | Abs | Abs |
| Calves | Calves | Calves | Calves |
| Triceps Pushdown | Back Extensions | Shoulder Press | 1 Leg Squat |
| Incline Bench | Lunges | Bench Press | Leg Extension |
| Dips | Squat | Bicep Curl (Bar) | Leg Curl |
| Preacher Curl | Leg Press | Seated Rows | Power Cleans |
| t-Bar Row | | Reverse Dips | |
| WEEKS 8–10 | | | |
| Abs | Abs | Abs | Abs |
| Calves | Calves | Calves | Calves |
| Incline Bench | Back Extensions | Bench Press | Leg Extension |
| Dumbbell Flys | Lunges | Hammer Curl | Leg Curl |
| Triceps Extensions | Squats | Lateral Raises | Power Cleans |
| Bicep Curl (Db) | Side Lunges | Tricep Pushdown | 1 Leg Squat |
| Upright Rows | Leg Press | Shoulder Press | |
| Lat Pulldowns (front) | | Shrugs | |

Following the training period of 10 weeks, the subjects were tested as for the pre-testing procedure. The performance measurements showed that subjects receiving D-Ribose increased the weight lifted once in the bench press by 10.5 pounds, while the placebo group improved by 10 pounds. The 1 RM Squat re-test showed a greater difference: 45.5 pounds for the ribose group versus 12 pounds for the placebo group. The body composition changed as follows:

TABLE II

Change in Body Fat Composition
Average percentage post training compared to percentage pre-training

| Treatment | Subject | Pre | Post | Difference |
|---|---|---|---|---|
| Skinfold Test, % Body Fat | | | | |
| Ribose | 3 | 16.6% | 14.2% | −2.4% |
| | 5 | 21.7 | 18.0 | −3.7 |
| | 8 | 14.8 | 11.5 | −3.3 |
| | 9 | 29.0 | 26.2 | −2.8 |
| Average | | | | −3.1% |
| Placebo | 4 | 20.6 | 23.3 | +2.6 |
| | 7 | 32.2 | 31.3 | −0.9 |
| Average | | | | −0.9 |

TABLE II-continued

Change in Body Fat Composition
Average percentage post training compared to percentage pre-training

| Treatment | Subject | Pre | Post | Difference |
|---|---|---|---|---|
| | Underwater Weight Test, % body fat | | | |
| Ribose | 3 | 17.7% | 18.5% | +0.8% |
| | 5 | 22.5 | 23.6 | −1.1 |
| | 8 | 17.5 | 12.5 | −5.0 |
| | 9 | 29.7 | 27.8 | −21.9 |
| Average | | | | −1.3% |
| Placebo | 4 | 23.9 | 22.8 | −1.1 |
| | 7 | 27.0 | 27.3 | −0.6 |
| Average | | | | −0.6 |

It can be seen from Table II that exercise has, in general, a benefit in reducing body fat and that over this ten week period, the supplementation with D-Ribose resulted in a faster decrease in body fat.. The skinfold test measures subcutaneous fat, a decrease in which results in the desired objective of greater muscle definition. The underwater weight test measures total body fat. In both parameters, the subjects given ribose achieved a greater decrease in body fat than those given placebo.

The performance measurements (more pounds lifted in the 1 RM tests) and differences in body weight indicated that muscle mass had increased. When the changes in body weight were determined, it was found that, on average, body weight increased an average of 3.4 pounds in the ribose group and remained the same in the placebo group. FIG. 1 illustrated the difference in lean body mass in the two groups.

EXAMPLE 2

Ribose Plus Creatine Administration in Humans

Ribose plus creatine, creatine alone or placebo will be administered to resistance-trained athletes and measurements of body weight, percent fat-free muscle mass, strength and stamina as in Example 1. Creatine acts as a high-energy phosphate bond reservoir in muscle tissue. Since its physiological action is not that of ribose, and since it has been shown that creatine administration increases muscle performance, it is expected that there will be an additive benefit in the decreasing of body fat when creatine is administered with ribose.

EXAMPLE 3

Ribose Plus L-carnitine Administration in Human Athletes

Ribose plus carnitine, carnitine alone or placebo will be administered to resistance-trained athletes and measurements of body weight, percent fat-free muscle mass, strength and stamina as in Example 1. Carnitine is useful for the mobilization of fatty acids, which can be metabolized to produce energy. Since its physiological action is not that of ribose, and since it has been shown that carnitine administration increases ATP production, it is expected that there will be an additive benefit in the decreasing of body fat when carnitine is administered with ribose.

EXAMPLE 4

Ribose Plus Pyruvate Administration in Human Athletes

Ribose plus pyruvate, pyruvate alone or placebo will be administered to resistance-trained athletes and measurements of body weight, percent fat-free muscle mass, strength and stamina as in Example 1. Pyruvate is an intermediate in the production of ATP. Since its physiological action is not that of ribose, and since it has been shown that pyruvate administration increases ATP production, it is expected that there will be an additive benefit in the decreasing of body fat when pyruvate is administered with ribose.

EXAMPLE 5

Ribose Plus Magnesium Administration in Human Athletes

Ribose plus magnesium, magnesium alone or placebo will be administered to resistance-trained athletes and measurements of body weight, percent fat-free muscle mass, strength and stamina as in Example 1. Magnesium has been shown to be important in muscle contraction. Since its physiological action is not that of ribose, and since it has been shown that magnesium administration enhances muscular contraction, it is expected that there will be an additive benefit in the decreasing of body fat when magnesium is administered with ribose

EXAMPLE 6

Ribose Plus Chromium Picolinate Administration in Human Athletes

Ribose plus chromium picolinate, chromium picolinate alone or placebo will be administered to resistance-trained athletes and measurements of body weight, percent fat-free muscle mass, strength and stamina as in Example 1.

All of the compositions and methods disclosed and claimed herein can be made and executed without undue experimentation in light of the present disclosure. While the compositions and methods have been described in terms of preferred embodiments, it will be apparent to those skilled in the art that variations may be applied to the compositions and methods described herein without departing from the concept and scope of the invention.

We claim:

1. A method comprising administering ribose to a human performing weight-training exercise in order to decrease the body fat of said human.

2. The method of claim 1 wherein the ribose is administered before and after weight-training exercise.

3. The method of claim 1 wherein the ribose is administered in a dose of about 0.5 to 40 gm.

4. The method of claim 1 wherein the ribose is administered in a dose of about 2 to 20 gm.

5. The method of claim 1 wherein the ribose is administered in a dose of about 3 to 8 gm.

6. A method for increasing the strength, percent fat-free muscle mass and stamina of a human compromising administering ribose and at least one supplement consisting of creatine, carnitine, pyruvate, magnesium or chromium picolinate.

* * * * *